United States Patent [19]

Van Dijk et al.

[11] Patent Number: 4,988,491

[45] Date of Patent: Jan. 29, 1991

[54] FLEXIBLE INTEGRATION OF THE PRODUCTION OF AMMONIA AND UREA

[76] Inventors: Christiaan Van Dijk, 10722 Glenway, Houston, Tex. 77070; Lowell D. Fraley, 703 Santa Maria, Sugarland, Tex. 77478

[21] Appl. No.: 336,658

[22] Filed: Apr. 11, 1989

[51] Int. Cl.$^5$ .................. G01C 1/04; G01C 273/04; G01C 273/10
[52] U.S. Cl. .................... 423/359; 423/356; 423/362; 564/66; 564/67; 564/69
[58] Field of Search .................. 564/66, 67, 69; 423/359, 362, 356

[56] References Cited

U.S. PATENT DOCUMENTS

| | | | |
|---|---|---|---|
| Re. 27,377 | 5/1972 | Otsuka et al. | 260/555 |
| 3,310,376 | 3/1967 | Cook et al. | 23/199 |
| 3,371,115 | 2/1968 | Cook et al. | 260/555 |
| 3,372,189 | 3/1968 | Otsuka et al. | 260/555 |
| 3,607,939 | 9/1971 | Kaasenbrood et al. | 260/555 A |
| 3,647,872 | 3/1972 | Kaasenbrood et al. | 260/555 A |
| 3,674,847 | 7/1972 | Kaasenbrood et al. | 260/555 A |
| 3,886,210 | 5/1975 | Mavrovic | 260/555 A |
| 3,929,878 | 12/1975 | Mavrovic | 260/555 A |
| 3,952,055 | 4/1976 | Mavrovic | 260/555 A |
| 4,012,443 | 3/1977 | Bonetti | 260/555 A |
| 4,013,718 | 3/1977 | Guadalupi | 260/555 A |
| 4,086,271 | 4/1978 | Mavorvic | 260/555 A |
| 4,088,685 | 5/1978 | Mavrovic | 260/555 A |
| 4,088,686 | 5/1978 | Mavrovic | 260/555 A |
| 4,094,903 | 6/1978 | Mavrovic | 260/555 A |
| 4,138,434 | 2/1979 | Lagana et al. | 260/555 A |
| 4,235,816 | 11/1980 | Lagana et al. | 564/72 |
| 4,291,006 | 9/1981 | Pagani et al. | 423/359 |
| 4,320,103 | 3/1982 | Pagani | 423/359 |
| 4,613,696 | 9/1986 | Zardi | 564/67 |

OTHER PUBLICATIONS

Douglas Keens, "Integrating Amonia and Urea Production", in I. Chem. E. Symposium, (Series No. 74) 1982.

*Primary Examiner*—Richard L. Raymond
*Assistant Examiner*—Peter G. O'Sullivan
*Attorney, Agent, or Firm*—Kirk, Bissex & Lindsay

[57] ABSTRACT

The process of the present invention which produces the flexible integration for the production of ammonia and urea uses adiabatic reforming of the carbonaceous feedstock such as natural gas. With adiabatic reforming of natural gas, a surplus of carbon dioxide is produced. With adiabatic reforming, substantially pure oxygen and nitrogen may be used which does not involve inert gases such as argon in the system. More importantly, adibatic reforming allows operation at much higher pressure than standard primary reforming, namely, between 700 and 3000 psig. When these pressures are used, the process includes a recycle of the methane and hydrogen from the ammonia synthesis loop to the adiabatic reformer.

The process of the present invention uniquely removes the carbon dioxide which is produced by the reforming of the carbonaceous feedstock and treatment by the watergas shift reaction in two independent stages. After the watergas shift, treatment of the ammonia synthesis gases is carried out preferably with a physical solvent, which removes at low cost most of the carbon dioxide. The remaining carbon dioxide is removed by reaction with ammonia, either hot or cold, respectfully leading to the production of ammonium carbamate, or ammonium carbonate.

The process of the present invention, further, is characterized by making a significant change in operation upon obtaining the message that the urea plant has to be turned down or shut down for a short period of time.

23 Claims, 2 Drawing Sheets

FLEXIBLE INTEGRATION OF THE PRODUCTION OF AMMONIA AND UREA

FIELD OF THE INVENTION

The present invention is directed to an integrated plant for the production of ammonia and urea. More specifically, the present invention involves a flexible integration of the production of ammonia and urea such that the ammonia production may be continued when short turn downs or repairs are being made to the urea reactor or plant.

BACKGROUND OF THE INVENTION

The present invention is directed to a process for loosely integrating an ammonia and a urea plant, starting from a carbonaceous feedstock like methane, naphtha, or coal.

The integration of ammonia and urea manufacture has been proposed many times before; however such proposed integrations, while seemingly attractive, have serious disadvantages, primarily because the proposed integrations were non-flexible or required the turn down or stoppage of operation of both the ammonia and urea plants when problems occured in one of the plants. The present proposal combines ammonia and urea manufacture in an attractive way, but allows independent operation of the ammonia plant, when the urea plant has to be turned down or taken off stream for necessary maintenance.

Commercially ammonia commonly is synthesized from methane via steam reforming in two stages. The first stage of reforming is done in a primary reforming furnace and the heat is supplied indirectly by burning methane. This is followed by the second stage of reforming which is carried out in a secondary reformer where the heat is supplied by injection of an amount of air into the effluent gas stream from the primary reformer The amount of air injected contains the amount of nitrogen which corresponds to the amount of nitrogen necessary to combine with the hydrogen produced in the reforming stages for the production of ammonia desired to be made and for the necessary bleed stream. After the reforming steps the reformed gas ($H_2$, $N_2$, $CO_2$ CO and small amounts of $CH_4$ and Ar) is contacted with a shift catalyst to convert the carbon monoxide with the excess steam into carbon dioxide and hydrogen. This shift reaction is carried out at increasingly lower temperatures. After cooling the gas down and removing condensed water, carbon dioxide is removed, preferably by absorption in a physical solvent. The remaining gas is warmed up and contacted with a methanation catalyst to convert the remaining traces of carbon monoxide and dioxide into methane, consuming some of the hydrogen in the gas stream. The treated gas, referred to as ammonia synthesis gas ($H_2$, $N_2$, $CH_4$ and Ar), is compressed and fed into the ammonia synthesis section. There it is commonly combined with an ammonia-containing recycle. The gas stream from the ammonia reactor is refrigerated to recover ammonia and at the same time traces of water, the ammonia catalyst being extremely sensitive to water. After proper preheat the gas is contacted with the ammonia catalyst, normally in a quench-type reactor. Most of the effluent is recycled via a recycle compressor, but some is bled out as purge gas, this to achieve a reasonable level of inerts like methane and argon in the ammonia reactor.

The most capital-intensive pieces of equipment of this complicated sequence are the primary reformer, the carbon dioxide extraction system, the compressors, the refrigeration system and to a lesser degree the ammonia reactor.

Such ammonia synthesis plants have the characteristic, that they are difficult to start up, because of their complexity, but once on stream, they can generally keep running for fifteen to twenty months between scheduled shutdowns. Start up is measured in days.

A commercial urea manufacturing facility is conventionally found adjacent to an ammonia plant. This urea plant uses as part of its feed the substantially atmospheric carbon dioxide extracted from the reformed gas usually by solvent extraction. Multi-stage compression is used to bring this carbon dioxide to urea reaction pressure. The other feed to the urea plant is part of the ammonia made in the ammonia plant. Even when maximal production of urea is desired, often some ammonia can not be converted to urea, because the amount of carbon dioxide, formed in the reforming of methane is insufficient for conversion of all of the ammonia produced in the ammonia plant to urea.

Normally ammonia and carbon dioxide are fed to the urea reactor, where they initially react or combine to generate liquid ammonium carbamate and heat. The heat, generated by this reaction, serves to elevate the temperature of the carbamate to urea reaction temperature where urea and water are formed. By proper heat exchange, the heat of this first stage (carbamate formation) can also be made partly available to a later point in the urea reactor, where lower temperatures will occur, due to heat demand of the carbamate conversion reaction which forms urea and water. From the final liquid stream unconverted ammonium carbamate and excess ammonia are removed by flashing and distillation, first at reaction pressure, if stripping is used, and then at increasingly lower pressures. The recovered gases are fed back into the inlet of the urea reactor, either in the form of gas or as condensed liquids. The remaining concentrated urea solution is evaporated and prilled.

Many variations in urea plant design exist; however a particularly attractive design is disclosed in U.S. Pat. Nos. 3,886,210; 3,929,878; 3,952,055; 4,086,271; 4,088,685; 4,088,686 and 4,094,903, all assigned to Urea Technology. In the process disclosed is a very effective use of the heat of carbamate formation in the first stage of reaction Further, the flash products, obtained at intermediate pressure by flashing the urea reactor effluent, are washed to remove the water content of the gases. To these gases containing ammonia, $CO_2$ is added, about 40% of the $CO_2$ at the lower pressure of the flash, which results in condensing the flashed ammonia as ammonium carbamate for liquid recycle. A large reduction of the compression duty of $CO_2$ is realized over other designs.

While the urea reactor proper is costly, a significant fraction of the total capital of the urea plant is found in the carbon dioxide compression.

As to operation, the start up of a urea plant is somewhat easy because of the uncomplicated reaction scheme of a urea plant, especially when helped by computer control Proper care has to be taken, but the plant can be in operation a short while after start up. Start up is measured in hours The urea plant, however, is characterized by a relatively large number of interruptions in the operation. One cause, for instance, may be due to handling streams which have the possibility of forming solids or another may be due to the possible change in conditions which may cause slight corrosive attacks.

An article 'Integrating Ammonia and Urea Production' by Douglas Keens in I. Chem. E. Symposium, (series number 74) in 1982, which is incorporated herein by reference in its entirety, discloses a number of proposals for the solid integration of ammonia and urea production. In each of the proposals however the integration is not flexible, and does not provide for a turn down or shut down of the urea production while continuing the production of ammonia.

U.S. Pat. No. 4,012,443; 4,013,718; 4,138,434; 4,235,816; 4,291,006; and 4,320,103 have been assigned to Snam Progetti S.p.A.

U.S. Pat. No. 4,012,443 discloses washing the ammonia reactor exit gases with an aqueous stream, thus recovering a concentrated ammonia stream. This stream is then used to absorb carbon dioxide out of the raw synthesis gas, which has been compressed to a pressure sufficing for both the ammonia and the urea reaction. The ammonium carbamate formed in the urea reactor is heated forming urea and some of the water and all the unreacted ammonia and carbon dioxide are recycled.

U.S. Pat. No. 4,138,434 discloses the use of the raw ammonia synthesis gas as stripping medium of the urea reactor effluent. It also uses waterwash to recover ammonia out of the ammonia reactor effluent. The raw synthesis gas is compressed up to both ammonia and urea synthesis pressure.

U.S. Pat. No. 4,235,816 also discloses water wash recovery of ammonia and ammonia wash of the raw synthesis gas. The cleaned up synthesis gas is then used for some more urea stripping. Again the pressure level chosen is suited for both ammonia and urea.

U.S. Pat. No. 4,291,006 describes an apparatus wherein the carbon dioxide is removed by absorption in a bottom heat-exchanged section, while the top secton is a normal countercurrent contactor. The absorber is disclosed as operating at urea reaction pressure.

U.S. Pat. No. 4,320,103 discloses a process which absorbs all of the carbon dioxide out of part of the raw ammonia synthesis gas and is specifically directed to a method which consists in the synthesis gas comprising carbon dioxide being fed to the carbon dioxide absorption unit in a specified manner.

U.S. Pat. Nos. 3,310,376 and 3,371,116 are assigned to Chemical Construction Corporation. The first, discloses the reaction of the carbon dioxide in the raw ammonia synthesis gas with pure ammonia to produce urea directly. In the second, the raw synthesis gas is mixed with the ammonia reactor effluent to remove the carbon dioxide.

Two patents assigned to Mitsui Toatsu Chemicals Inc., namely U.S. Pat. No. Re 27,377 and U.S. Pat. No. 3,372,189, both disclose methods wherein the compressed raw ammonia synthesis gas is reacted with ammonia, recovered as such from the ammonia reactor. This absorption reaction is operated at or above urea synthesis pressure. The second patent, carries out the absorption of carbon dioxide at conditions, which lead to a molar ratio of ammonia to carbon dioxide in the liquid between 2.0 and 3.6. The absorbate is then fed at lower pressure to the urea reactor.

Stamicarbon N. V. has three patents, all assigned by Kaasenbrood et al., namely U.S. Pat. No. 3,607,939; U.S. Pat. No. 3,647,872 and U.S. Pat. No. 3,674,847. In the first patent, an ammonia solution recovered from the ammonia reactor effluent by waterwash, which concentrated aqueous ammonia solution may possibly also contains urea, is used to recover carbon dioxide. The second patent, not only washes out the ammonia, but then strips it with an inert gas stream, which is then fed to the urea reactor. In the third patent, the raw ammonia synthesis gas is used for stripping of the urea reactor effluent and then fed to the ammonium carbamate reactor.

While the discussed patents show more or less seemingly attractive ways to integrate ammonia and urea plants, they all suffer from a very serious shortcoming. As mentioned before, the urea facility rather frequently has to be shut down or turned down for some minor maintenance. Normally the urea plant is back on stream within 4 or up to 24 hours. As the urea plant start up is fast, these interruptions do not greatly affect the total production of a urea plant However, coupling such a urea operation with a large ammonia plant as disclosed in the practices set forth in the patents would result in the necessity of shutting down the ammonia plant, together with the urea plant, whenever maintenance problems for the urea plant occured. Restarting the ammonia plant, however, due to its complexity, can take as much as three days. A substantial loss of productivity for the total complex is then the result. As the capital cost of the complex is much larger than that of the urea plant alone, the resulting financial loss is substantial The fear of integrating the ammonia plant and urea plant has kept the industry from following the suggestions made heretofore on this subject.

In the Keens review mentioned hereinabove, the author arrives at the conclusion that the integration of an ammonia and urea plant results in a 10% capital reduction. He finally concludes: 'It is curious, that full integration of the two processes have not yet taken place on an industrial scale....' The conclusion must be that the suggested integrations heretofore suggested in general suffer serious shortcomings.

In the integration of an ammonia plant and a urea plant heretofore, it is been advocated to absorb the carbon dioxide from the raw ammonia synthesis gas and at the same time convert the carbon dioxide and ammonia into ammonium carbamate. The absorption of the carbon dioxide with an ammonia solution is usually done in a vessel which provides heat exchange (cooling) as the reaction of the carbon dioxide and ammonia to form ammonium carbamate is exothermic. The temperatures in the absorption vessel may range from 220° to 360° F. Furthermore, while adiabatic reforming in and of itself is not a new process, all the examples and discussions regarding an integrated ammonia-urea process are obviously based on the standard combination of primary and secondary reforming. One of the deficiencies of a process which uses primary and secondary reforming of natural gas is that it often produces a gas with insufficient carbon dioxide for all the ammonia produced to be converted into urea, so that an excess amount of ammonia is always produced which must be disposed of or sold.

SUMMARY OF THE INVENTION

The process of the present invention which produces the flexible integration for the production of ammonia and urea uses adiabatic reforming of the carbonaceous feedstock such as natural gas. With adiabatic reforming of natural gas, a surplus of carbon dioxide is produced with adiabatic reforming, substantially pure oxygen may be used which does not involve inert gases such as argon in the system. More importantly, adiabatic reforming allows operation at much higher pressures than standard primary reforming, namely, between 700 and 3000 pounds per square inch gauge (psig). In the process of the present invention a preferred operation is carried out at a sufficiently high pressure that the pressure used in the preparation of the ammonia synthesis gas approaches or is at the pressures used in the ammonia sector or reactor, namely, pressures within the range of 1500 to 3000 psig and preferrably between about 1700 and 2500 psig. When the high pressure adiabatic reforming of the present invention is used, the process includes a recycle of the methane and hydrogen in the ammonia loop purge to the adiabatic reformer and under such conditions, the carbonaceous feed, oxygen and nitrogen are of low argon content. This recycle allows reuse of part of the methane left unconverted in the reformer as generated in the methanator, simultaneously, recouping valuable hydrogen and operating conditions which otherwise would result in significant increase of the energy used per ton of ammonia or urea made. The process of the present invention eliminates a number of the expensive process units normally advocated in the integrated ammonia-urea plant.

The process of the present invention uniquely removes the carbon dioxide which is produced by the reforming of the carbonaceous feedstock and treatment by the watergas shift reaction in two independent stages. After the watergas shift, treatment of the ammonia synthesis gases is carried out preferably with a physical solvent, which removes at low cost most of the carbon dioxide. The remaining carbon dioxide is removed by reaction with ammonia, either hot or cold, respectfully leading to the production of ammonium carbamate, or ammonium carbonate.

The process of the present invention, further, is characterized by making a significant change in operation upon obtaining the message that the urea plant has to be turned down or shut down for a short period of time Upon receiving this message or signal, provisions are made to store ammonia, usually as a concentrated aqueous liquid, or by reacting the ammonia with the carbon dioxide and produce only ammonium carbonate. This is easily accomplished by if necessary increasing the flow of water being added to the aqueous ammonia stream used in the absorption of the carbon dioxide and, additionally, cooling to temperatures within the range of about 100° to about 180° F., so that the resulting reaction product of ammonia and carbon dioxide becomes mostly a solution of ammonium carbonate and not a melt of ammonium carbamate. A solution of ammonium carbonate can at these lower temperatures be easily stored. Thus the ammonia plant keeps operating, generating an aqueous solution of ammonium carbonate, possibly also liquid aqueous ammonia, for as long as the urea plant is down. When the urea plant again becomes operational, the added water stream (and extra cooling) is discontinued and the product of the carbon dioxide and ammonia results in ammonium carbamate or smaller amounts of ammonium carbonate which are fed to the urea sector. Immediately after restart of the urea sector, some of the recycle streams from the urea sector may not be available and certain adjustments are required until the integrated operation is steady. Thereafter, a small stream of the stored ammonium carbonate solution may be added as a small fraction of the liquid stream which is the feed to the urea sector.

BRIEF DESCRIPTION OF THE DRAWING

For a detailed description of the present invention and a preferred embodiment thereof, reference will made to the accompanying drawing wherein.

DETAILED DESCRIPTION OF THE INVENTION

Figure 1:
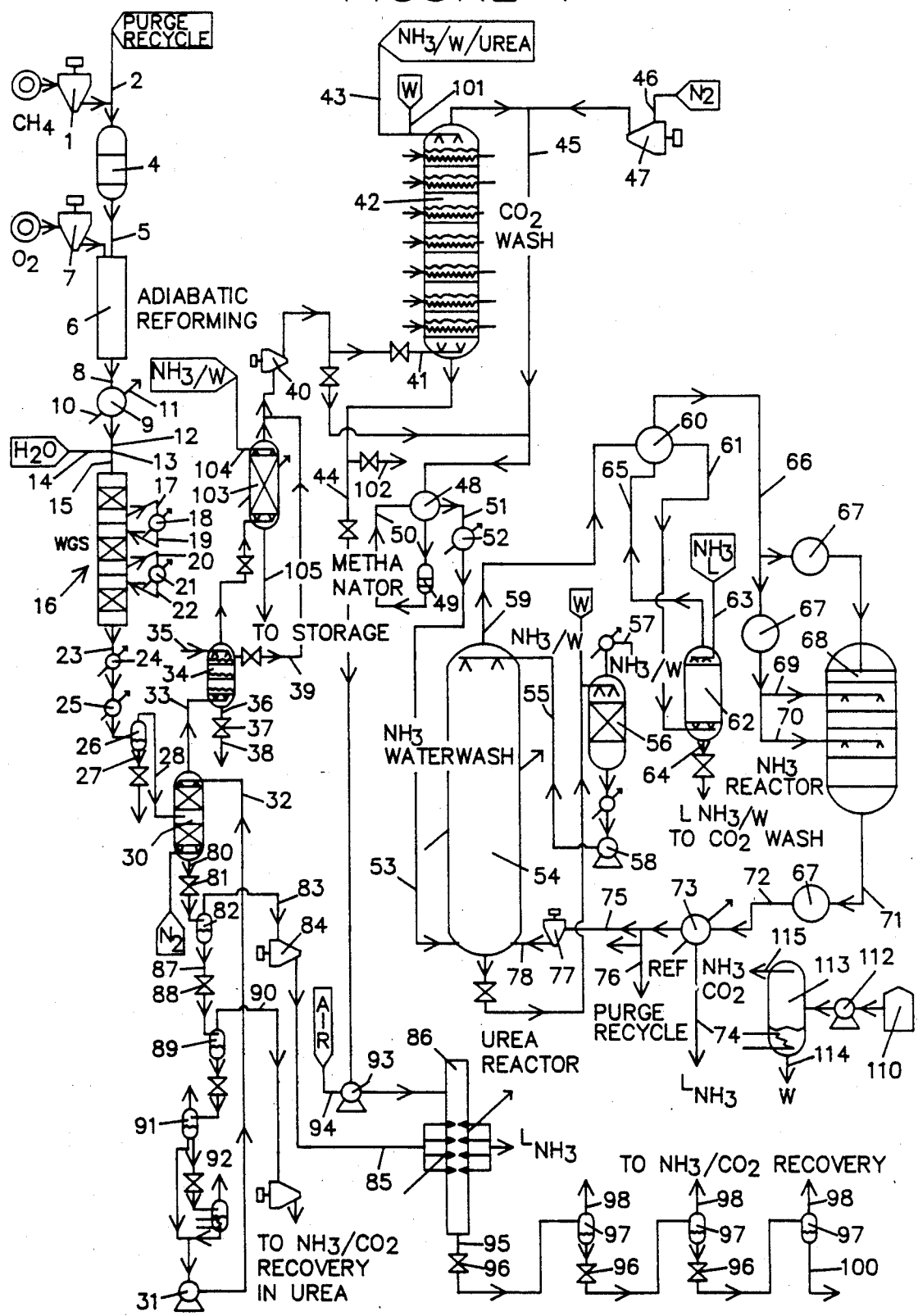
FIG. 1 is a schematic process flow sheet for the flexible integration of the production of ammonia and urea.

The present invention is directed to the production of urea as the predominant product of a flexibly integrated plant for the production of ammonia and urea. There are several specific flowsheets which may be used to accomplish the flexible integration; however, the process of the present invention has certain significant features which not only permit the integration but provide a process with a substantial capital savings.

The process of the present invention eliminates the high capital cost of primary and secondary reforming and instead uses adiabatic reforming. Instead of primary or adiabatic reforming at pressures of 300 to 600 psig, pressures used in the production of ammonia, the process of the present invention uses adiabatic reforming at pressures in excess of 700 psig, preferrably 1500 to 3000 psig and most preferrably 1700 to 2500 psig. The oxygen containing gas used in the adiabatic reforming must be compressed to the operating pressure Preferably pure argon-free oxygen is added to the adiabatic reformer An argon-free oxygen contains less than 0.5% by volume argon. At the higher pressure ranges, compression of the natural gas may also be necessary.

It is preferred to operate the adiabatic reforming step with oxygen alone. The nitrogen necessary for the production of ammonia is added later, preferably after the removal of carbon dioxide and, when necessary, after compression to the ammonia reaction pressure Further it is preferred to use argon-free nitrogen In the air separation process used to obtain the oxygen and nitrogen, it is relatively easy to separate nitrogen and argon by distillation. The advantage of using argon-free nitrogen is that the build-up of inerts is mostly limited to methane. An argon-free nitrogen contains less than 0.1% by volume argon. Most of the bleed stream out of the ammonia synthesis loop can be recycled to the inlet of the adiabatic reformer thus saving for internal use valuable methane and hydrogen. A small purge or bleed takes care of any traces of argon entering with the natural gas and/or oxygen, which purge can be used for fuel.

The effluent stream from the adiabatic reformer is cooled by heat exchange with water with the large production of steam. Water is also injected into the still hot gas effluent stream from the adiabatic reformer, wherein the water becomes steam. Treatment of the gas, in multiple stages of watergas shift process units, convert the carbon monoxide by reaction with the steam into carbon dioxide and additional hydrogen. At the higher pressure ranges, more than one watergas shift process unit may be used. It is preferred to remove carbon dioxide between watergas shift units.

The process of the present invention has several distinctions from the conventional ammonia-urea plant in the handling of the carbon dioxide. First, due to the higher pressures of the gas the removal of the carbon dioxide is easy by simple solvent extraction. A simple adiabatic contact with a suitable solvent permits removal of most of the carbon dioxide from the gas effluent from a watergas shift process unit. However, heretofore in the combined ammonia-urea plants all the carbon dioxide was advocated to be removed by reaction with an ammonia solution to produce the desired ammonium carbamate. In the process of the present invention, it is preferred to remove a major amount of the carbon dioxide by means of a solvent extraction which is used as feed to the urea sector and the remaining carbon dioxide, 3 to 50%, is removed by contacting the gas with an ammonia solution, producing either ammonium carbamate or carbonate It is preferred to have the absorption of $CO_2$ carried out with a solvent countercurrently in a short tower. The entering solvent still contains significant amounts of carbon dioxide The removal of the carbon dioxide at the operating pressures used permits two or three $CO_2$ flashes, starting at higher than atmospheric pressure The last $CO_2$ flash, at about atmospheric pressure, removes any excess $CO_2$ unnecessary to the production of urea, while the first or first two flashes remove part of the $CO_2$, necessary for the urea manufacture, at appreciable pressure. The $CO_2$ compression, normally used and necessary to raise the $CO_2$ pressure up to urea reaction pressure, is thus substantially reduced. This variant can utilize the $CO_2$ and $NH_3$ reaction (the carbamate heat of formation) to supply the heat for the conversion of carbamate into urea in the urea reactor.

Because of the danger of compressing carbon dioxide-containing raw synthesis gas which is possibly contaminated by ammonia, the process of one process flow sheet of the present invention has a wash operation normally operating at small flow prior to the gas entering the compressor. An instrument warning will be generated on ammonia building up in the bottom water layer, due to formation of ammonium carbonate. Waterflow will then increase, to keep the ammonia concentration down to very low values. An instrument warning in the top tray will give warning to take adequate steps to diminish the ammonia contamination and possibly, even shut the compressor down, when too high a concentration of ammonium carbonate is reached in that tray.

The raw ammonia synthesis gas, if not already at sufficiently high pressure, is then compressed up to ammonia synthesis pressure, about 1500 to 3000 psig, preferably within the range of about 1700 and 2500 psig. This pressure range is substantially lower than the preferred pressure range for the urea manufacture, which is from 3000 to 5000 psig. It is noted that the pressure used to produce the ammonia in the integrated processes advocated heretofore was at a pressure within the range of 3000 to 5000 psig.

In an alternate process flow sheet, a second watergas shift process unit may follow the solvent extraction of the $CO_2$ and the remaining $CO_2$ is removed in a concentrated ammonia wash before the compression of the raw ammonia synthesis gas. The raw ammonia synthesis gas is then compressed to ammonia synthesis pressure, if necessary, which may take place after methanation which converts any carbon monoxide or carbon dioxide to methane.

In the process of the present invention only a small compression of the raw ammonia synthesis gas suffices when the pressures as disclosed herein are selected In case a high adiabatic reaction pressure and a low ammonia synthesis pressure is used, compression of the raw ammonia synthesis gas may even be completely eliminated, in which case the earlier described water wash before compression to remove ammonia is not necessary. If the feed to the urea plant is part ammonium carbamate, this solution is pressurized to the higher pressures used in the urea reactor with a liquid pump. Thus, the $CO_2$ compression is less than integrated processes advocated heretofore, because the initial pressure of the $CO_2$ is higher and the amount of $CO_2$ requiring compression to the higher pressures used in the urea production is smaller.

After compression, the raw ammonia synthesis gas containing some carbon dioxide is then contacted with a strong aqueous solution of ammonia to absorb the remaining carbon dioxide and form ammonium carbamate, which solution also may contain minor amounts of urea to improve ammonium carbamate solubility. After the absorption step, it is preferred to add the nitrogen. The combined gases pass through a methanation unit before being introduced to the ammonia synthesis loop.

The most preferred operation for the ammonia synthesis loop of the integrated plant is at pressures within the range between 1700 and 2500 psig, a pressure about the same as or somewhat lower than the presently advocated lowest pressure for ammonia synthesis, using a standard iron ammonia catalyst Such a low pressure, especially when combined with the relatively high pressure preferred for the adiabatic reforming, results in a very low energy of compression for the raw ammonia synthesis gas. As mentioned before, it may even be possible to eliminate the compression of the raw ammonia synthesis gas to the ammonia synthesis loop altogether. At the lower range of pressures used for ammonia synthesis in the process of the present invention, it is advocated to use ruthenium on carbon catalyst, as proposed by British Petroleum in Great Britian patent No. 2034194 or German patent NO. 2748972, which allows a higher ammonia concentration to be reached, due to activity of the catalyst at lower than normal temperatures.

If high pressure is used for the adiabatic reforming reaction, namely 1500 psig or higher, a high percentage of the carbon dioxide present after multi-step watergas shift is removed in a first contact with a physical solvent. This can be followed by a second watergas shift treatment and a second treatment with a physical solvent. The remaining carbon dioxide then can be as small as 3% or less of the stoichiometric amount of carbon dioxide reacted with ammonia to produce urea in the integrated plant. This small amount of carbon dioxide preferably is removed by reaction with aqueous ammonia to a solution of ammonium carbonate, exiting at temperatures between 100° and 180° F. This solution can be fed as such to the urea reactor, but it is preferred to heat this solution at higher than atmosphere pressure under reflux, and obtain gaseous ammonia and carbon dioxide together with a little steam, which stream can be condensed to pumpable ammonium carbamate, for feed to the urea reactor.

The synthesis gas remaining after the three stages of carbon dioxide removal is cooled, preferably with cold cooling water, to remove the ammonia Nitrogen is added at the pressure of the synthesis gas in the proper stoichiometric amount to react with the hydrogen to form ammonia. Then the synthesis gas is warmed and contacted with a methanation catalyst to remove the remaining traces of carbon monoxide and carbon dioxide which are converted into methane.

The ammonia synthesis gas is then introduced into the ammonia synthesis loop. When the gas has been contacted with an ammonia stream where more than a trace of ammonia may be in the gas, the ammonia synthesis gas is combined with the recycle gas from the ammonia reactor via ammonia condensation and recycle compressor, and the combined gas streams are countercurrently contacted with an aqueous stream, containing about 5 to 15% ammonia, under cooling by either cooling water at higher pressure, or by cooled cooling water at the preferred pressure range of about 1500 to 2500 psig. A concentrated aqueous ammonia stream is obtained. The water, used in the ammonia absorber, is preferably obtained out of one or another of the recycle streams in the urea sector of the plant, but for solubility reasons should be low in carbonate. The fresh water used should be low in soluble salts. After the gas stream has been washed, it still will contain a small amount of ammonia due to the presence of ammonia in the absorption fluid. The ammonia synthesis gas may have been compressed before the carbon dioxide wash or just before introduction to the ammonia synthesis loop. In one alternative, the ammonia synthesis gas is combined with the recycle gas after the aqueous ammonia wash in the ammonia synthesis loop. The ammonia synthesis gas is then cooled by heat-exchange to a temperature of between 0° and 5° F. The remaining gas is already practically dry, when it is finally countercurrently contacted with a cold liquid ammonia stream. Evaporation of some of the ammonia results in cooling of the gas by about 10° to 15° F., thus providing a ready stream for the heat exchange of the earlier gas stream. Any ammonia recovered after countercurrent waterwash is used in the carbon dioxide removal vessel. By distillation of the aqueous ammonia, practically dry ammonia can be obtained directly with a small but significant amount of water, between about 0.5 and 3%.

The ammonia synthesis gas stream then is fed to an ammonia reactor. On contact with the catalyst ammonia is formed, with a resulting temperature increase. A quench ammonia reactor is preferred. The exit gas stream from the ammonia reactor contains, depending upon conditions, between 10 and 15 % ammonia. That ammonia effluent stream is cooled with cold cooling water It is possible, even at the lowest pressure in the pressure range used to produce ammonia, to condense part of the ammonia as liquid ammonia. This liquid ammonia is partly used for deep cooling of the gas stream, being dried by cooling to remove water, entering the ammonia reactor. A bleed is taken out of the ammonia effluent gas stream. Most of this bleed is recycled to the inlet of the adiabatic reformer. A small amount is purged to stabilize the level of argon in the ammonia synthesis loop. From this small purge ammonia is recovered, for instance by waterwash before the remaining gas is vented. The rest of the ammonia effluent gas stream is then compressed in a recycle compressor and mixed with the earlier mentioned raw ammonia synthesis gas stream after the methanator.

The absorption step of the remaining carbon dioxide with aqueous ammonia has been found according to the present invention to give flexibility to the integration of the ammonia and urea plants. When the urea sector of the integrated plant has to be shut down, or turned down, extra water is added to the absorption and more cooling is applied, so that a solution of ammonium carbonate results instead of a solution of ammonium carbamate. When this condition occurs, the ammonium carbonate solution is preferably fed to storage instead of feeding to the urea reactor.

When the urea reactor or sector is back on stream, a small amount of the ammonium carbonate solution may be fed to the urea reactor, together with the larger amount of ammonium carbamate solution and excess ammonia from normal operation The ammonium carbonate may also be introduced into other streams as a liquid or may be distilled. When the carbonate solution is distilled the carbonate is formed into the carbamate by removal of water or more generally into ammonia and carbon dioxide for introduction into the absorption vessel or fed to the urea reactor.

The combined ammonium carbamate or carbonate solution and excess ammonia liquid feed is pressurized by a pump to the urea reactor at a pressure within the range of between about 3000 and 5000 psig. A small amount of air may be added to suppress corrosion. As a consequence of this extra feed of ammonium carbonate the urea sector must have a slightly higher capacity for conversion than if only ammonium carbamate were added to this sector. As the overall downtime of the urea section is small, only relatively small amounts of ammonium carbonate solutions are involved. The theoretical increase of capacity of the urea sector may be less than 5 % and the cost of this increased capacity is small when considering the increased flexiblity obtained.

It is recognized that the proposed solution does not hold, when unexpectedly the urea sector might go down for a long period, several weeks, for instance. It is not expiendent to provide the plant with sufficient storage to store the ammonium carbonate production for such a long period But it is recognized, that most of the common urea sector interruptions have little or no effect on the production capabilities of the ammonia sector of the integrated ammonia-urea plant.

While these are the most advantageous improvements as compared to earlier schemes of integration of an ammonia and urea plant, the process of the present invention also has many other advantages and new elements, which will become apparent by a more detailed discussion of the operation with reference to the drawings.

Refering now to FIG. 1., natural gas enters the process via a line (CH$_4$) at a pressure between 700 and 3000 psig or is compressed in compressor 1 to a pressure between 700 and 3000 psig, preferably between 1500 and 3000 psig, and most preferably between 1700 and 2500 psig. A small amount of hydrogen-containing gas, available from the bleed stream, is admixed with the natural gas via line 2. A small amount of steam may also be added to the gas stream by line 2. The mixed gas stream enters a vessel 4 for the cleanup of any traces of sulfur compounds in the natural gas Vessel 4 contains a zinc oxide sandwich to remove the sulfur compounds. The cleaned gas stream is then preheated (not shown) and fed via line 5 to an adiabatic reforming reactor 6 Also fed to the adiabatic reforming reactor 6 is a stream of oxygen-containing gas which is compressed by compressor 7 to the same pressure as the cleaned gas stream fed to the adiabatic reforming reactor 6. This oxygen-containing gas may be pure oxygen or oxygen which contains nitrogen, or this stream can be formed by mixing oxygen and air. In the reforming reactor 6 a temperature may be reached between 2100 and 2700° F. The effluent gas from the reforming reactor 6 exits via line 8 and is introduced into heat exchanger 9. The water introdued into heat exchanger 9 by line 10 is formed into high pressure steam and removed by line 11. Quenching the reforming effluent with water can also be used (not shown). The cooled gas then passes via line 12 to a point 13, where it is mixed with water, being fed in via line 14. Steam is adiabatically generated and the gas mixture is fed via line 15 to a three stage watergas shift unit 16. The gases are contacted in a first bed of shift catalyst in the top of the unit 16 and then pass via line 17 to a cooler 18 and back via line 19 to the next chamber of the unit 16 which contains a second bed of shift catalyst. The shift reaction, which is the reaction of CO and $H_2O$ to form $CO_2$ and $H_2$, is repeated in the second bed. The gases are removed via line 20, cooled in cooler 21, and reintroduced by line 22 into a third bed of shift catalyst The gases then are removed from the watergas shift unit 16 via line 23. The gases are then cooled by passing through a first heat exchanger 24 and a second heat exchanger 25. Medium pressure steam is produced in heat-exchanger 24. The cooled gases then are introduced into a separation vessel 26, where water condensate is removed via line 27.

In the integration of an ammonia plant and a urea plant heretofore, either all of the carbon dioxide has been removed as is done in the production of ammonia or it has been advocated to absorb the carbon dioxide from the raw ammonia gas and at the same time convert the carbon dioxide and ammonia into ammonium carbamate. In the process of the present invention, however, it is advocated to remove any excess $CO_2$ (excess meaning that amount of $CO_2$ in excess of the stoichiometric amount which will combine with ammonia to form urea) and in addition at least 50% of the $CO_2$ needed for the urea production by solvent extraction and remove the remaining $CO_2$ by reaction of ammonia to produce either ammonium carbamate or ammonium carbonate. The gas stream from the separation vessel 26 is then fed via line 28 to a simple or countercurrent solvent extraction contactor 30. The removal of excess carbon dioxide and that carbon dioxide which is to be fed to the urea sector is removed in contactor 30. This contact preferably is carried out with a physical solvent, like Selexol (a trademark process of Norton Chemical Company which is described in Hydrocarbon Processing, 1988, p. 72 and incorporated herein by reference) which is fed in by pump 31 via line 32. The amount of $CO_2$ removed by the solvent extraction will depend on the pressure used in the reforming step. The gas stream out of contactor vessel 30 is fed via line 33 to an ammonia safe guard chamber 34. This chamber 34 is a multi-tray vessel with water on each tray. When the ammonium carbonate concentration in the bottom tray rises above a predetermined level, additional water will be added through line 35 and solution taken out through line 36, valve 37, and line 38. The gas after this contact with water to remove any ammonia in the gases in chamber 34 is fed via line 39 to raw synthesis gas compressor 40. The pressurized gas is fed via line 41 to a countercurrent contractor 42, where the carbon dioxide still remaining in the gases reacts with ammonia, fed to this contactor unit 42 in aqueous solution via line 43. During normal operation, that is when both the ammonia and the urea synthesis sectors of the plant are operative, most of the water in the aqueous ammonia is derived from recovered water out of the urea sector. Then the carbon dioxide is converted into ammonium carbamate in solution, which solution is taken out via line 44. The temperatures in the absorption contactor unit 42 will vary with the pressure. If high pressures approaching the pressures used in the urea sector are employed the carbamate produced in the absorption unit 42 will be close to urea reaction temperatures, which are between 340° and 390° F. However at the pressures advocated in the present process which are essentially at the ammonia producing pressure, the temperatures will not be higher than about 220° to 280° F. It is possible to treat the ammonia synthesis gas at pressures high enough so that compression is not necessary before introducing the gases to the absorption unit 42 and only a small amount of $CO_2$ is then converted into ammonium carbonate in unit 42. It is also possible to operate the washing in vessel 42 at lower temperatures and with more water feed, resulting in production of ammonium carbonate solution. This solution can be pumped to a vessel 113 where heat is used to liberate carbon dioxide and ammonia at desired operating pressures Then gases are fed to the ammonia/carbon dioxide receiving section of the urea sector as will be described in more detail hereinafter.

The raw ammonia synthesis gas exiting unit 42 via line 45 may contain ammonia and possibly some water taken over from the absorption unit 42. Pure nitrogen is added through line 46 and compressed to the pressure of the gas by compressor 47. The combined gases are fed via line 45 to exchanger 48, where the combined gases are heated to methanation temperature of about 650° F. and contacted with a methanation catalyst in vessel 49. The effluent gas, warmed up by the methanation reaction, is then fed to the other side of the earlier mentioned heat-exchanger 48 via line 50. The cooled gas is then fed via line 51 to a second heat exchanger 52. The gas is then ready to be fed via line 53 into ammonia absorber 54. Here the gas may be combined with the ammonia recycle stream which will be described in detail hereinafter and contacted with an aqueous stream of ammonia. This aqueous stream enters vessel 54 via line 55. In vessel 54 cooling is provided by precooled cooling water which is cooled by evaporation, induced by steam jet. This is a well-known operation (not shown) for obtaining cooling water of temperatures as low as 50° to 60° F. Very low pressure steam can be used for this cooling of cooling water. The ammonia solution is removed from vessel 54 and concentrated by flashing at reduced pressure in a flash tank 56 In this way a concentrated ammonia solution containing less than 3% water is obtained. This solution exits via line 57. The remaining liquid is removed from tank 56 and cooled and pumped by pump 58 to the top of vessel 54 for contacting the combined gas streams. Additional water may be added as necessary to the flash loop in the line between vessel 54 and 56.

The effluent gas stream which includes the ammonia synthesis recycle gas stream from which most of the ammonia has been removed in the ammonia scrubber vessel 54 is removed overhead via line 59 and then first cooled by heat-exchange against cold gas, by entering the heat-exchanger 60. The cooled gas is then introduced via line 61 to a vessel 62 where the gas is scrubbed countercurrently with liquid ammonia introduced via line 63. This scrubbing with liquid ammonia removes esentially all the water in the gases and the aqueous ammonia formed in the vessel 62 is removed via line 64. The temperature of the scrubbed gases is now down to about minus 10° F. The scrubbed gases exit vessel 62 via line 65 to heat-exchanger 60 where the cooled gases are heated. The ammonia synthesis gases are then passed via line 66 to a heat-exchanger 67. Part of the gas is heat-exchanged up to ammonia reaction kick-off temperature in heat-exchanger 67, and that portion enters the top of ammonia reactor 68. That portion of gas then is contacted with an ammonia catalyst in the first bed of ammonia reactor 68. The rest of the gas may be heat-exchanged to an intermediate temperature in another part of heat-exchanger 67 and introduced after the first catalyst contact via lines 69 and 70 to reduce the temperature and allow further reaction over the second and third catalyst beds in ammonia reactor 68. Finally the gas stream, now containing from 10 to 15 % ammonia, depending upon conditions, is fed back via line 71 to the earlier mentioned heat-exchanger 67 to provide the heat to the incoming gases. The ammonia reactor effluent gas is then fed via line 72 into heat-exchanger 73, where the ammonia reactor effluent gas is cooled by cold cooling water, as before obtained by evaporation, induced by a steam jet The condensed liquid ammonia is taken out via line 74. This liquid ammonia may be used in several ways, one of which is as the liquid ammonia introduces into line 63 for removal of water in the ammonium synthesis gas. The cooled gas continues via line 75 to a point, where a small bleed stream is taken via line 76. When the nitrogen, entered via line 46 is substantially argon-free, most, that is between 50 and 95%, of this bleed stream is fed back to the inlet line 2. When normal amounts of argon are present, only a small amount of the bleed is returned to line 2. The cooled gas is fed via line 75 to recycle compressor 77 and fed into vessel 54 via line 78. This completes a description of the ammonia synthesis loop and the ammonia sector of the integrated amonia-urea plant of the present invention.

To complete the description of the integrated ammonia-urea plant and process of the present invention it is necessary to return to several points in the ammonia making process to decribe the details of the interfaces with the urea sector of the integrated plant. The first interface with the urea sector is the removal of $CO_2$ from the reformed gases. The first removal of $CO_2$ is with solvent extraction in vessel 30. The $CO_2$ enriched solvent is removed from vessel 30 via line 80 and passed through pressure let-down valve 81 to a first flashtank 82, where part of the carbon dioxide in solution is liberated and fed via line 83 to $CO_2$ compressor 84 and thence via line 85 to urea reactor 86. The liquid from first flashtank 82 is fed via line 87 through flash valve 88 to a second flash vessel 89, where more $CO_2$ is flashed and removed via line 90. Additional stages of flashing may occur in vessel 91 and the remaining liquid is then introduced into pump 31. A small part of the liquid stream is fed to vessel 92, where it is heated (not shown) to drive out absorbed water. The $CO_2$ flashed and needed for the production of urea is split into two streams. About 40% of the total urea equivalent is compressed to the pressure of the urea recovery section (pressures in the range of 275 to 400 psig) where ammonia is stripped from the urea product and is added to this ammonia to form ammonium carbamate which is then returned to the urea reactor 86. The rest of the $CO_2$ is compressed up to the urea reactor pressure, which can be about 3000 to 4000 psig., and is added to the reactor 86 with ammonia which forms carbamate and heat to produce the urea.

Coming back to the liquid made in vessel 42 and exiting via line 44, this liquid is added to the urea sector and specifically the urea reactor 86 by means of liquid pump 93. To this pump 93 is also fed a small quantity of air via line 94 to suppress corrosion. The urea reactor 86 is kept at the preferred temperature of between about 360° and 395° F. by indirect heating with condensing steam of 235 psig pressure, or by injection of $CO_2$. After reaction of the ammonium carbamate at about 3000 to 4500 psig the concentrated urea liquid exits through line 95. The liquid is passed through a series of pressure let-down valves 96 and introduced into a series of flash vessels 97 with heat input in the later vessels were at the lower pressure ammonia and carbon dioxide are generated and separated from the liquid in vessels 97. The gases are fed to recovery (not shown) via lines 98. The final concentrated urea liquid exits via line 100 for final evaporation and urea prilling (not shown).

When the urea sector has to be stopped or is stopped, fresh salt-free water is added to the ammonia solution via line 101 introduced into the vessel 42. The product of reaction in the vessel 42 then is not ammonium carbamate, but ammonium carbonate. As this compound is quite soluble in water, a concentrated solution can be obtained even at low ambient temperature. Storage of this solution then is available via line 102. An alternative is to employ a vessel which is placed before the compressor 40. Vessel 103 can be then used for the total gas flow or a similar larger vessel can be used for this function. Thus upon stoppage of the urea sector, the ammonia sector continues in operation. The valve in line 39 is closed as well as in line 41 and all the gas passes into vessel 103. Added water may be introduced, for example, via line 104 in vessel 103 so as to produce ammonium carbonate which is removed via line 105 while still removing essentially all the $CO_2$ and ammonia before compressing the ammonia synthesis gas and passing it directly to line 45. In addition the $CO_2$ compressors in line 83 and 90 are shut down and if $CO_2$ is removed from vessel 30 it may be vented. Alternatively, pump 31 is shut down leaving more $CO_2$ to be removed in vessel 103.

Figure 2:
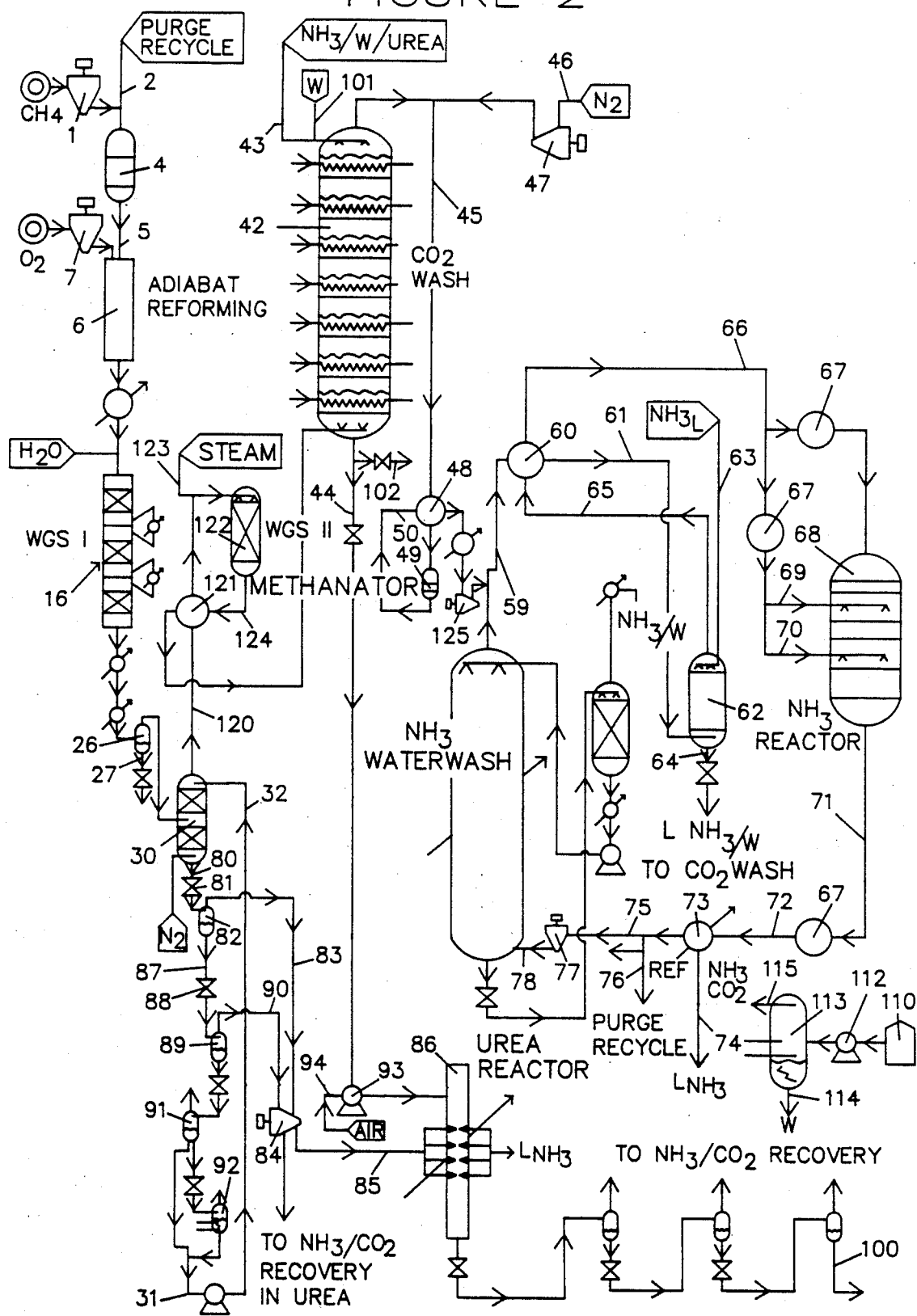
FIG. 2 is a second schematic process flow sheet for a preferred embodiment of a process for the flexible integration of the production of ammonia and urea.

In the urea sector of FIG. 1, referred to as $NH_3/CO_2$ recovery, is a storage vessel 110 Storage vessel 110 will store all of the ammonium carbonate which is produced, especially when the urea sector is not in operation because of being shut down or turned down. When the urea sector is back in operation, the ammonium carbonate solution may be pumped from storage vessel 110 by pump 112 into an ammonium carbonate stripping unit or vessel 113. The ammonium carbonate solution is heated in vessel 113 to remove the water. Water is removed from the bottom of the vessel 113 via line 114 whereas the ammonia and carbon dioxide formed is removed overhead via line 115. This overhead stream may be condensed with steam to form ammonium carbamate for introduction into the urea reactor 86 or may be added in other various vessels. Referring now to FIG. 2 the same reference numerals will be used to designate the like structures or vessels as in FIG. 1. This flow sheet illustrates a process when the pressure in the adiabatic reforming reactor 6 is essentially at or just slightly above or below the pressure to be utilized in the ammonia synthesis loop. At these high pressures, use of low argon feeds becomes more important as a larger recycle based upon low argon levels, allows more methane in the raw synthesis gas. After the carbonaceous feed has been reformed in adiabatic reforming reactor 6 the effluent gas is treated with steam in the first watergas shift unit 16. This unit may have several stages The effluent from the first watergas shift unit 16 is cooled and water is condensed in vessel 26 with the water removed via line 27. The gas is then introduced into vessel 30 where it is treated with an extractive solvent introduced via pump 31 and line 32. The treated gas is removed by line 120 where it is heated in a heat exchanger 121 before introducing into a second watergas shift unit 122. Additional steam may be added by line 123. With the pressures being in the range of 1500 to 3000 psig, a single watergas shift unit may not convert all of the carbon monoxide to carbon dioxide even in several stages. The effluent from the second watergas shift unit 122 is removed by line 124 and is cooled in the heat exchanger 121 before introduction to the $CO_2$ wash unit 42. The remaining carbon dioxide which may be only 3 to 10% is removed in the ammonia water wash in vessel 42. The aqueous product produced may be ammonium carbonate and sent to the storage vessel 110 via line 102. The ammonia synthesis gas is removed by line 45 at which point nitrogen introduced via line 46 in compressor 47 is added in the proper stoichiometric amount. The combined gases are heated before passing through methanator 49 wherein the gas is removed by line 50 and exchanged with the introductory gases in exchanger 48 before cooling and introduction into line 59 of the ammonia synthesis loop where the raw ammonia synthesis gas (fresh feed) and the ammonia synthesis recycle gas stream are combined A compressor 125 may be used for the fresh feed if compression is necessary from the pressures used in the front end of the ammonia sector as compared to the ammonia synthesis loop. It is this compressor 125 which may, when the pressures are balanced, be eliminated or in the alternative be a relatively small compressor as compared to the normal size compressor used in the production of ammonia.

Also in FIG. 2 it is noted that in the handling of the carbon dioxide that a single compressor may be used since the carbon dioxide is recovered at such high pressures. The solvent which extracts the carbon dioxide from vessel 30 is removed via line 80 and passed through a pressure reduction valve 81 into a flash vessel 82. The $CO_2$ removed via line 83 may be at pressures far in excess of the usual $CO_2$ removal processes which are near atmospheric pressure and may be introduced to compressor 84 where greatly reduced compression is necessary to compress the carbon dioxide for introduction via line 85 to the urea reactor 86. Likewise, the flash of carbon dioxide in the second flash vessel 89 via line 90 can be introduced to the same compressor 84 or alternatively a separate compressor may be used for compression of the carbon dioxide either for use in the urea reactor or in the recovery section where the $NH_3/CO_2$ is recovered. The third flash vessel 91 is set to remove any access carbon dioxide and that carbon dioxide may simply be vented to the atmoshpere. Part of the solvent is introduced into vessel 92 which is heated to remove water that may accumulate in the solvent before the solvent is recirculated through pump 31 via line 32 through the absorption to the extraction vessel 30.

In the two flow sheets of the FIGS. it is illustrated that the location of the compressor for compressing the ammonia synthesis gas to the pressure necessary for the gases to be introduced into the ammonia synthesis loop may be located either before the $CO_2$ wash (FIG. 1) when substantial amounts of carbon dioxide are still in the gas and ammonium carbamate is to be produced or just prior to the introduction into the ammonia synthesis loop when small amounts of remaining carbon dioxide are in the ammonia synthesis gas and the operation is at high pressures.

The process of the present invention will be further described by the following examples.

EXAMPLE 1

The feed to a combined ammonia-urea plant consists of a natural gas stream, containing 2880 mol per hour (MPH) methane, which stream is available at 1050 psig. The stream is compressed to 1200 psig and combined with a recycle containing 96 MPH methane, 405 MPH hydrogen, 145 MPH nitrogen, and 9 MPH argon. The combined gases are contacted with a zinc oxide sandwich, which serves to remove the last traces of hydrogen sulfide and related compounds The combined gas is then fed to an adiabatic reformer. Also added to the adiabatic reformer is 2031 MPH of oxygen, containing 1 MPH argon. The reforming reaction results in an effluent gas stream at 2500° F. from the adiabatic reformer, consisting of 2793 MPH carbon monoxide, 158 MPH carbon dioxide, 5354 MPH hydrogen, 953 MPH steam, 24 MPH methane, and 10 MPH argon. This gas is cooled in a heat exchanger, generating with heat exchange with water about 9500 MPH 1800 psig steam from the heat exchanger. Water is then injected into the cooled gas stream to cool the gas further to about 650° F. before being introduced into a first contact with a watergas shift catalyst. The injected water, having turned to steam, serves as reactant to convert the carbon monoxide to carbon dioxide and hydrogen by the watergas shift reaction. The watergas shift unit has two addional stages, with the final temperature being 450° F. A total of 5680 MPH water has been added, of which 3901 MPH remain in the gas as steam. The rest of the gas composition is 60 MPH carbon monoxide, 289 MPH carbon dioxide, 8095 MPH hydrogen, 145 MPH nitrogen, 24 MPH methane, and 10 MPH argon.

The effluent gas from the watergas shift unit is cooled in a heat exchanger, indirectly producing by heat exchange with water 5 psig low-pressure steam from the heat exchanger. The effluent gas is further cooled and the steam is condensed. Water is separated from the cooled gas, after which the cooled gas enters the carbon dioxide extraction section or unit. Here the cooled gas is countercurrently contacted in a short tower with almost three theoretical plates with about 1,136 gallons per minute (gpm) Selexol solvent, containing about 127 MPH $CO_2$. Selexol is a trade name for the dimethyl ester of polyethylene glycol used in the process of Norton Chemical Company. In the countercurrent contact of the cooled gas about 1,662 MPH $CO_2$ are absorbed into the solvent. The effluent gas stream is removed at the top of the tower and the Selexol liquid stream is removed from the bottom. A first portion of the Selexol liquid stream is flashed at 153 pounds per square inch absolute (psia) and a gas stream of about 662 MPH $CO_2$ is taken off at the top of the flash drum. The liquid is flashed again at 70 psia and a second $CO_2$ stream of about 567 MPH $CO_2$ is produced from the second flash drum. A final flash of the remaining liquid is taken at 15 psia, where 433 MPH $CO_2$ are released and discarded in the normal operation, when the urea plant is operating steadily. The Selexol solvent is pumped back to the countercurrent tower for pressurized absorption of $CO_2$.

The 567 MPH $CO_2$ are compressed to 153 psia and mixed with the 662 MPH $CO_2$ flashed at this pressure The combined stream is compressed in a series of steps to 4100 psig and fed to the urea reactor system. There it is combined at different points with ammonia, generating heat, which serves to compensate for the heat of reaction of ammonium carbamate to urea.

After this partial carbon dioxide removal the gas is compressed to 2200 psig. Then it enters the final carbon dioxide removal contactor. For absorption are used different streams, namely the concentrated ammonia aqueous ammonia solution, available from the treatment of the ammonia reactor exit gas and the fresh feed gas, to which ammonia had been added. A further important stream is the aqueous solution of ammonia (and some carbon dioxide), returning from the cleanup of the flashed gases in the urea sector of the plant. When these last gases are not available because the urea sector is not operating, an excess amount of 7,000 MPH salt-free water is used instead. After an earlier shutdown of the urea sector a small bleed, containing about 700 MPH of water and a corresponding amount of ammonium carbonate, out of the ammonium carbonate storage, is the final stream fed to the afore-mentioned contactor. Normally the carbon dioxide is absorbed mainly as ammonium carbamate in a very concentrated solution, also still containing excess ammonia, water and possibly urea During the urea shutdown, however, sufficient clean water has been added to arrive with more cooling than before at a cooler ammonium carbonate solution, which still may have surplus ammonia in it.

The ammonium carbamate solution is pumped up to 4100 psig, together with a small amount of air, added for protection against corrosion. The stream is heated up to 380° F. and enters the urea reactor. During the reaction the stream is further heated by appropriate $CO_2$ injections, to obtain a substantially constant temperature in this reactor. The effluent of the urea reactor is flashed twice to remove excess ammonia and unreacted ammonium carbamate. Finally the solution is flashed in vacuo and fed to final flashing and prilling.

Out of the final carbon dioxide absorber the gas exits with about 60 MPH carbon monoxide, 10 MPH carbon dioxide, 8095 MPH hydrogen, 145 MPH nitrogen, 1500 ammonia, 10 MPH water, 24 MPH methane, and 10 MPH argon. This gas is heat-exchanged to about 650° F. and contacted with a methanation catalyst In this contact carbon mono- and di-oxide are converted into methane with some of the hydrogen present. The effluent now contains about 80 MPH water. The gas is cooled down, first in the last heat-exchanger mentioned, then by cooling with cooling water. Condensate is then removed.

The gas is cooled with cold cooling water of about 60° F. to condense ammonia at a temperature of about 70° F. Condensed ammonia is separated. Now the gas is mixed with the recompressed recycle of the ammonia exit stream (see later) The combined stream is counter-currently contacted with aqueous ammonia under cooling by cooling water of 60° F, obtained by evaporating water, which evaporation is induced by a steam eductor. It is advantageous to carry out this evaporation, while the water is being used in a heat-exchanger. This results not only in a lower actual water temperature in the heat exchanger, but also improves the heat transfer coefficient. Concentrated aqueous ammonia is obtained for use in the earlier mentioned final carbon dioxide absorption. The gas exits with about 3.5 % ammonia still present. The gas stream is cooled by heat-exchange against cold gas, followed by evaporating liquid ammonia. The final temperature is −10° F. Several times during this cooling condensed liquids are being removed. The final gas is sufficiently dry to enter the ammonia reactor. The gas composition at this point is 33093.9 MPH hydrogen, 11,660.5 MPH nitrogen, 6,120.6 MPH methane, 572 MPH argon, and 783.5 MPH ammonia. First the cold gas is used for heat-exchange and then split into two streams The smaller stream is heat-exchanged to about 650° F. and fed to the first stage of the ammonia reactor. The other part of the gas stream is heat-exchanged to about 400° F. and used for quenching the hot effluent of the catalyst contact down for further reaction. After three or four catalyst contacts the gas is taken out Its composition at this point is 25740.9 MPH hydrogen, 9,209.5 MPH nitrogen, 6,120.6 MPH methane, 572 MPH argon, and 5,678.6 MPH, or 12% ammonia. The gas is used for heat-exchange against the incoming gas streams and fed to a heat-exchanger, where it is cooled with 60° F. cooling water to condense liquid ammonia. About 1,459.3 MPH ammonia are thus liquefied. A bleed stream is taken, containing 450 MPH hydrogen, 161 MPH nitrogen, 107 MPH methane, and 10 MPH argon, next to the corresponding amount of ammonia. This bleed stream is washed with an aqueous stream to recover contained ammonia. Of this bleedstream 90% is returned to the front end of the process and the remaining 10% is purged out. Then the main gas stream is fed to a recycle compressor and combined with the incoming fresh feed, as mentioned above.

COMMENTS ON EXAMPLE 1

On shutdown of the urea sector the $CO_2$ left after the Selexol contact and compression has to be absorbed with ammonia into a solution, that can be stored. This is achieved with the added amount of water and cooling. Ammonium carbonate is storable at ambient conditions at concentrations up to 50%. As this does not consume all the ammonia (because example 1 takes part of the stoichiometric amount of $CO_2$ out with Selexol and compresses that), the rest of the ammonia has to be stored one way or the other. A small storage is available for liquid ammonia, but not too much of liquid ammonia remains after use for recovery of ammonia and drying of the gas. Ammonia can be stored as 30 to 40 % aqueous solution with not too much vapor pressure It is also possible to route some of the compressed $CO_2$ to the unit, where the gas, containing $CO_2$ is washed with ammonia, thus making more ammonium carbonate for storage.

EXAMPLE 2

The feed to a combined ammonia-urea plant consists of a natural gas pipeline stream, containing 2634.8 MPH methane, 93.8 MPH $C_2H_6$, 24.6 MPH $C_3H_8$, 5.4 MPH $C_4H_{10}$, 0.3 MPH $C_5H_{12}$, 0.3 MPH $CO_2$, 11.3 MPH A, and 55.1 MPH $N_2$. which stream is available at 800 psig. The stream is compressed to 1100 psig and combined with a recycle containing 66.7 MPH methane, 320 MPH hydrogen, 106.7 MPH nitrogen, and 42 MPH argon. The combined gases are contacted with a zinc oxide sandwich, which serves to remove the last traces of hydrogen sulfide and related compounds. The gas is then preheated to 900° F. and fed to the adiabatic reformer There it is mixed with 1915 MPH oxygen, also containing 9.7 MPH A. The resulting reaction results in a gas stream at 2500° F., consisting of 2834 MPH carbon monoxide, 122.1 MPH carbon dioxide, 5319 MPH hydrogen, 752.4 MPH steam, 162.1 MPH $N_2$, 63.0 MPH A, and 30 MPH $CH_4$. This gas is cooled in a heat exchanger, generating about 8000 MPH superheated 1800 psig steam. Then water is injected to cool the gas down to about 650° F. for a first contact with a watergas shift catalyst The injected water, having turned to steam, serves as reactant to convert the carbon monoxide. This is twice repeated with the final temperature being 450° F. A total of 6675 MPH water has been added, of which 3901 MPH remain in the gas as steam. The rest of the gas composition is 60 MPH carbon monoxide, 2896.1 MPH carbon dioxide, 8093 MPH hydrogen 162.1 MPH nitrogen, 63 MPH argon and 30 MPH $CH_4$.

The gas is cooled, indirectly producing 20 psig low-pressure steam. The condensed water is separated, after which the gas enters the carbon dioxide extraction sector. Here the gas is contacted in a short countercurrent operation with about 2295 gpm Selexol solvent. Selexol is a trade name for the dimethyl ester of polyethylene glycol used in the process of Norton Chemical Company. About 2408.4 MPH carbon dioxide are absorbed and removed from the solvent by flashing in a series of flashings. The first flash is at 157 psia and 975.5 MPH $CO_2$ are liberated. This stream is compressed to 3200 psig and fed to the urea reactor. The second flash is at 60 psia and also 975.5 MPH $CO_2$ are evolved. This stream is compressed to 300 psig and fed to the urea recovery sector, where it reacts with evolved gaseous ammonia This results in formation of liquid ammonium carbamate and production of heat, which is used in the evaporation of unreacted chemicals in the urea reactor exit stream. The final flash is at atmospheric and 457.4 MPH $CO_2$ are bled out. After this flash the Selexol is returned to the first contactor by a pump. A small amount of Selexol is taken out and dried by heating and stripping to balance the water content.

After this partial carbon dioxide removal the gas is compressed to 2200 psig. Then it enters the final carbon dioxide removal contactor. For absorption are used different streams, namely liquid ammonia, then some of the concentrated ammonia aqueous ammonia solution, available from the treatment of the ammonia reactor exit gas and the fresh feed gas, to which ammonia had been added. A further important stream is the aqueous solution of ammonia and carbon dioxide, returning from the cleanup of the flashed gases in the urea sector of the plant. When the urea sector is not operating, an excess amount of 10,000 MPH salt-free water is used instead. After an earlier shutdown of the urea sector a small bleed, containing about 70 MPH of water and a corresponding amount of ammonium carbonate, out of the ammonium carbonate storage, is the final stream fed to the afore-mentioned contactor. Normally the carbon dioxide is absorbed mainly as ammonium carbamate in a very concentrated solution, also still containing excess ammonia, water and possibly urea. During the urea shutdown, however, sufficient clean water has been added to arrive at a cooler ammonium carbonate solution, which still may have surplus ammonia in it.

The ammonium carbamate solution is pumped up to 3200 psig, together with a small amount of air added for protection against corrosion. The stream is heated up to 380° F. and enters the urea reactor. Another stream of ammonium carbamate is fed to the urea reactor from the recovery sector, where at about 300 psig $CO_2$ has reacted with recovered ammonia gas, to give liquid ammonium carbamate. Also are fed the rest of the $CO_2$ and excess liquid ammonia. The reaction of ammonia and $CO_2$ serves to further heat the reactants to obtain a substantially constant temperature in this reactor. The effluent of the urea reactor is flashed twice to remove excess ammonia and unreacted ammonium carbamate. Finally the solution is flashed in vacuo and fed to final flashing and prilling.

Out of the final carbon dioxide absorber the gas exits with about 60 MPH carbon monoxide, 10 MPH carbon dioxide, 8093 MPH hydrogen, 162.1 MPH nitrogen, 1500 ammonia, 10 MPH water, 30 MPH methane, and 9 MPH argon. This gas is heat-exchanged to about 650° F. and contacted with a methanation catalyst In this contact carbon mono- and di-oxide are converted into methane with some of the hydrogen present. The effluent now contains about 80 MPH water. The gas is cooled down, first in the last heat-exchanger mentioned, then by cooling with cooling water. Condensate is then removed.

The gas is cooled with cold cooling water of about 60° F. to condense ammonia at a temperature of about 70° F. Condensed ammonia is separated. Now the gas is mixed with the recompressed recycle of the ammonia exit stream (see later) The combined stream is countercurrently contacted with aqueous ammonia under cooling by cooling water of 60° F, obtained by evaporating water, which evaporation is induced by a steam eductor. It is advantageous to carry out this evaporation, while the water is being used in a heat-exchanger. This results not only in a lower actual water temperature in the heat exchanger, but also improves the heat transfer coefficient. Concentrated aqueous ammonia is obtained for use in the earlier mentioned final carbon dioxide absorption. The gas exits with about 3.5% ammonia still present This gas stream is cooled by heat-exchange against cold gas, followed by evaporating liquid ammonia. The final temperature is $-10°$ F. Several times during this cooling condensed liquids are being removed. The final gas is sufficiently dry to enter the ammonia reactor. The gas composition at this point is 33093.9 MPH hydrogen 11,660.5 MPH nitrogen, 6,120.6 MPH methane, 572 MPH argon, and 783.5 MPH ammonia. First the cold gas is used for heat-exchange and then split into two streams The first stream is heat-exchanged to about 650° F. and fed to the first stage of the ammonia reactor. The other part of the gas stream is used for quenching the hot effluent of the catalyst contact for further reaction. After three or four catalyst contacts the gas is taken out Its composition at this point is 25740.9 MPH hydrogen 9,209.5 MPH nitrogen, 6,120.6 MPH methane, 572 MPH argon, and 5,678.6 MPH (or 12 %) ammonia. The gas is used for heat-exchange against the incoming gas stream, further cooled with coo ling water and then fed to a heat-exchanger, where it is cooled with 60° F. cooling water to condense liquid ammonia. About 1,459.3 MPH ammonia are thus liquefied. A bleed stream is taken, containing 480 MPH hydrogen, 160 MPH nitrogen, 100 MPH methane, and 63 MPH argon, next to the corresponding amount of ammonia. This stream is washed with an aqueous stream to absorb the ammonia. Then ⅔ is returned to the front end of the process and the remaining ⅓ is purged. After the bleedstream has been removed the remaining gas is fed to a recycle compressor and combined with the incoming fresh feed, as mentioned above.

EXAMPLE 3

The feed to a combined ammonia-urea plant consists of a natural gas stream, containing 2559.9 MPH methane, 91.1 MPH ethane, 23.9 MPH propane, 5.2 MPH butane, 0.3 MPH pentane, 0.3 MPH $CO_2$, 55.6 MPH $N_2$, and 1.0 MPH A. This stream is available at 800 psig. The stream is compressed to 1800 psig and combined with a recycle containing 126.0 MPH methane, 432 MPH hydrogen, 144 MPH nitrogen, and 22.5 MPH argon. The combined stream is preheated to 900° F. The combined gases are contacted with a zinc oxide sandwich, which serves to remove the last traces of hydrogen sulfide and related compounds. Now the gas is fed to the adiabatic reformer. There it is treated with 1866 MPH oxygen, compressed up from 450 psig feed level, which oxygen also contains 1.5 MPH A. The resulting reaction results in a gas stream at 2500° F., consisting of 2761 MPH carbon monoxide, 111.1 MPH carbon dioxide, 5312 MPH hydrogen, 708.2 MPH steam, 197.4 MPH nitrogen, 25 MPH A, and 90 MPH methane, at a pressure of 1750 psig. This gas is cooled in a heat exchanger, generating about 14000 MPH preheated 1800 psig steam. Then water is injected to cool the gas down to about 650° F. for a first contact with a watergas shift catalyst. The injected water, having turned to steam, serves as reactant to convert the carbon monoxide. The gas is cooled down and contacted again with a watergas shift catalyst. This is repeated with the final temperature being 450° F. A total of 4300 MPH water has been added, of which 1675 MPH remain in the gas as steam. The rest of the gas composition is 136.7 MPH carbon monoxide, 2735.4 MPH carbon dioxide, 7936.3 MPH hydrogen, 197.4 MPH nitrogen, 25 MPH argon, and 90 MPH methane.

The gas stream is cooled indirectly producing 50 psig steam. Then it is fed to a heat-exchanger to warm up the gas after the first Selexol treatment. The gas is cooled and condensed water separated, after which the gas enters the carbon dioxide extraction sector. Here the gas is countercurrently contacted with at first 700, later increased to 1,400 gpm Selexol solvent, containing before contact with any gas 44 MPH $CO_2$. Selexol is the trade name for the dimethyl ester of polyethylene glycol used in the process of Norton Chemical Company. About 2732 MPH $CO_2$ are absorbed into the solvent. The Selexol liquid stream is taken out and first flashed at 165 psia. 1174.4 MPH $CO_2$ are taken off. The liquid is then flashed at 33 psia. Another 1174.4 MPH $CO_2$ are released. A final flash is taken at 15 psia, where 393.4 MPH $CO_2$ are released, together with 400 MPH $N_2$, which is used to strip the Selexol in the bottom of the flash vessel. A small bleed of 4000 pounds per hour (#/Hr) is taken for heating and stripping to remove picked up water, which small stream is then combined with the main stream. Half of the Selexol is fed to the above mentioned extraction. The rest of the Selexol stream is fed to the extraction, described below.

The low-pressure 1174.4 MPH $CO_2$ are compressed to 310 psia and fed to the urea recovery section, where the gas is reacted with ammonia evolved there. The heat of reaction to ammonium carbamate is used as process heat to help recover unreacted species from the urea reactor effluent. The carbamate is pumped into the urea reactor. The $CO_2$, developed at 165 psia, is compressed to 3100 psig, and fed to the inlet of the urea reactor. There it is combined at different points with ammonia, generating heat, which serves to compensate for the heat of reaction of ammonium carbamate to urea.

The main raw synthesis gas now still contains about 136.7 MPH CO and 100 MPH $CO_2$. This gas stream after initial warmup is further heat-exchanged against the main part of the gas stream during cooling of that stream in the first set of watergas shift operations. Water is injected into the gas stream during this heat-exchange so that steam is generated. The gas exits from this heat exchange at a temperature of about 400° F. with a steam content of 700 MPH. This gas is fed to a low-temperature watergas shift catalyst. Out of this contact the gas consists of 40 MPH CO, 196.7 MPH $CO_2$, 8033 MPH $H_2$, 197.4 MPH nitrogen, 90 MPH of methane, and 25 MPH argon. After cooling the gas is contacted with half of the Selexol recycle. After the $CO_2$ level is reduced down to 100 MPH the Selexol stream is taken out and fed to the appropriate mixing point in the earlier mentioned Selexol absorption step.

After this partial carbon dioxide removal the gas is contacted with a slight excess of ammonia under cooling and an about 50 wt. % solution of ammonium carbonate is taken off. This solution is warmed up at 340 psia and the ammonium salt is decomposed into ammonia and $CO_2$. Cooling results in formation of molten ammonium carbamate, which is fed to the urea reactor together with only minor amounts of water. In the main synthesis gas only 10 MPH $CO_2$ remains.

After this last removal of $CO_2$ the gas is mixed with argon-free nitrogen in order to obtain a hydrogen to nitrogen ratio of 3/1. The gas is warmed up by heat-exchange and fed to the methanator. After cooling condensate is removed ad the gas is fed to the ammonia loop without being compressed. The composition of the gas at this point (after having taken a loss of 40 MPH hydrogen) is 7833 MPH $H_2$, 2611 MPH $N_2$, 25 MPH A, 140 MPH $CH_4$, and 8 MPH water vapor. This gas, ammonia synthesis gas, is fed directly to the ammonia synthesis loop without forward compression.

In the ammonia synthesis loop, ammonia is removed by a water wash of the recycle gas stream in an ammonia waterwash vessel. The aqueous ammonia removed from the ammonia waterwash vessel is heated under a very modest reflux. In this way dry ammonia can be obtained, but it suffices to obtain for instance a 97/3 (by volume) mixture of ammonia and water since the ammonia is used in the production of urea.

The fresh feed, or ammonia synthesis gas hereinabove, is mixed with an ammonia synthesis recycle gas stream containing 25859.2 MPH $H_2$, 8619.7 MPH $N_2$, 1346.8 MPH A, 7542.3 MPH $CH_4$, and 438.1 MPH $NH_3$. The combined gas stream is heat exchanged down to a temperature of 0° F., condensed aqueous ammonia may be separated, and the gas is fed to a countercurrent contact with 900 MPH liquid ammonia. This final contact reduces the water content from a few parts per million down to the part per billion range. It also increases the ammonia content to 2% of total gas in the ammonia synthesis gas.

This gas stream is heated in portions in a heat exchanger and fed to the ammonia reactor. In the ammonia reactor a ruthenium type catalyst is used, which allows reaction at lower temperatures, thus achieving higher ammonia concentrations than would be possible with similar amounts of the standard iron type catalyst. As before part of the gas is warmed up to inlet temperature, which here is only 675° F. After reaction to about 875° F. cold gas is fed in as quench and the gas mixture, now at a temperature of 700° F., is fed to a second catalyst bed. This is repeated for a third bed with an inlet temperature of 710° F. The final gas composition is 26339.2 MPH $H_2$, 8779.7 MPH $N_2$, 1371.8 MPH A, 7682.3 MPH CH$_4$, and 6003.6 MPH NH$_3$. A 12% ammonia thus has been reached at a lower pressure than possible with similar ammoniates of a standard promoted iron-type ammonia catalyst.

After cooling by heat-exchange and with cooling water, the gas is cooled further by having cooling water of 60° F. in the heat-exchanger. 900 MPH ammonia is separated. A bleed stream is taken, containing next to the corresponding amount of ammonia 480 MPH H$_2$, 160 MPH N$_2$, 25 MPH A, and 140 MPH CH$_4$. Of this recycle 90% is fed back to the adiabatic reformer, while 10% is purged and used for fuel. The gas stream is compressed in the recycle compressor to about 1800 psig and then is fed to a countercurrent contact with 10 wt. % aqueous ammonia under cooling in the ammonia waterwash vessel. This reduces the ammonia content down to 1%. This is the recycle gas stream used for mixing with the incoming ammonia synthesis gas stream.

Part of the ammonia made and recovered in the ammonia synthesis loop is fed to the ammonium carbonate reactor. The rest of the ammonia is fed to the urea reactor to be used in combination with the CO$_2$.

COMMENTS ON EXAMPLE 3

On shutdown of the urea sector there are two possibilities for the continued operation of the ammonia sector. The first one is that the gas by-passes the Selexol treatment and is directly treated with sufficient aqueous ammonia. The resulting ammonium carbonate solution can be stored. This is achieved with the added amount of aqueous ammonia and increased cooling. Ammonium carbonate is storable at ambient conditions at concentrations up to 50%. A small storage is available for liquid ammonia, which is necessary for start-up purposes. The second possibility is to only make the amount of ammonium carbonate as under standard conditions, that is roughly 100 MPH. In that case ammonia has to be stored as 30 to 40% aqueous solution, which solutions do not have too much vapor pressure.

On restart of the urea sector the stored ammonium carbonate is fed to the ammonium carbonate stripping unit. That unit and the urea sector itself will therefore be slightly higher loaded than during normal operation. A design latitude has to be there to allow this slight overproduction. When most of the ammonia is stored as aqueous solution, the restart of the urea unit calls for more CO$_2$ to be reacted with ammonia. Less CO$_2$ is then discarded for a while till the aqueous ammonia is worked down.

Instead of operating with the ruthenium catalyst system it is also possible to achieve elimination of the forward compressor, using the iron type catalyst. With this standard catalyst, however, larger catalyst volumes are necessary, in order to attain sufficient ammonia levels in the reactor exit stream.

We claim:
1. A process for the flexible manufacture of ammonia and urea which comprises:
   adiabatically reforming a carbonaceous feedstock in a reformer with an oxygen containing gas in the preparation of an ammonia synthesis gas;
   introducing nitrogen gas to produce an ammonia synthesis gas which consists of hydrogen, nitrogen, traces of ammonia, methane and argon;
   said argon in said carbonaceous feedstock, oxygen containing gas and nitrogen being less than 0.2% by volume of those combined feedstock gases;
   removing a purge stream from the effluent of the ammonia reactor; and
   recycling most of said purge stream to said adiabatic reformer.

2. A process according to claim 1 wherein said adiabatic reforming is at a pressure between 700 and 3000 psig.

3. A process according to claim 1 wherein argon free oxygen and nitrogen are used in the process.

4. A process according to claim 1 wherein between 50 to 95% of the purge stream is recycled to the reformer.

5. A process for the flexible manufacture of ammonia and urea which comprises:
   reforming a carbonaceous feedstock at a pressure in excess of 700 psig in the preparation of an ammonia synthesis gas;
   extracting a part of the carbon dioxide from the raw ammonia synthesis gas;
   reacting the remaining carbon dioxide in the raw ammonia synthesis gas with aqueous ammonia to form a solution containing the reaction product of ammonia and carbon dioxide; and
   using said solution in the production of urea.

6. A process according to claim 5 wherein any excess carbon dioxide and at least 50% of the stoichiometric amount of carbon dioxide used in the production of urea is extracted by a physical solvent.

7. A process according to claim 6 wherein the carbon dioxide is removed from the physical solvent by at least two pressure reduction flashes.

8. A process according to claim 7 which further includes:
   compressing a portion of the flashed carbon dioxide to a pressure for addition to a urea reactor.

9. A process according to claim 7 which further includes:
   compressing a portion of the flashed carbon dioxide to a pressure for mixing with the ammonia flashed from the urea product.

10. A process according to claim 5 wherein the carbon dioxide reacted with ammonia forms an ammonium carbamate solution.

11. A process according to claim 10 which further includes:
    introducing said carbamate solution to a urea reactor.

12. A process according to claim 5 wherein the carbon dioxide reacted with ammonia forms an ammonium carbonate solution.

13. A process according to claim 12 which further includes:
    storing said ammonium carbonate solution.

14. A process according to claim 12 which further includes:
    introducing said ammonium carbonate solution to a urea reactor.

15. A process according to claim 12 which further includes:
    heating said ammonium carbonate solution to form ammonia and carbon dioxide.

16. A process for the manufacture of ammonia and urea which provides a flexible integration of the production of ammonia and urea when the urea reactor is turned down for any maintenance or repair, comprising:
    contacting part of the carbon dioxide formed in the production of ammonia synthesis gas with an ammonia solution and sufficient water to form a solution containing the reaction product of ammonia and carbon dioxide mainly as ammonium carbonate.

17. A process according to claim 16 wherein said solution is stored until said reactor is back on stream.

18. A process according to claim 16 which further includes:
introducing said ammonium carbonate solution to a urea reactor.

19. A process according to claim 16 which further comprises:
heating said ammonium carbonate solution to form ammonia and carbon dioxide.

20. A process according to claim 16 wherein said solution is used in the production of urea.

21. A process according to claim 1 which further includes:
treating the effluent gas stream from said adiabatic reformer in two watergas shift units.

22. A process according to claim 21 which further includes:
removing carbon dioxide from said gas stream after each of said watergas shift units.

23. A process for the flexible manufacture of ammonia and urea which comprises:
adiabatically reforming a carbonaceous feedstock in a reformer with an oxygen containing gas in the preparation of an ammonia synthesis gas;
treating the effluent gas stream from said adiabatic reformer in a watergas shift unit;
extracting a part of the carbon dioxide from the raw ammonia synthesis gas;
reacting the remaining carbon dioxide in the raw ammonia synthesis gas with aqueous ammonia to form a solution containing the reaction product of ammonia and carbon dioxide;
introducing said raw ammonia synthesis gas into an ammonia synthesis loop containing an ammonia reactor;
washing the effluent from said ammonia reactor with an aqueous ammonia stream for removing ammonia as an aqueous solution; and
using said solution containing the reactor product of ammonia and carbon dioxide and said aqueous ammonia solution in the production of urea.

* * * * *